United States Patent [19]

Biscar

[11] Patent Number: 4,752,284
[45] Date of Patent: Jun. 21, 1988

[54] ARTIFICIAL GRAVITY INTRACELLULAR MOLECULAR EXTRACTION

[76] Inventor: Jean P. Biscar, 1752 Coolidge, Apt. 203, Troy, Mich. 48084

[21] Appl. No.: 938,608

[22] Filed: Dec. 5, 1986

[51] Int. Cl.[4] .............................................. B04B 5/00
[52] U.S. Cl. .................................... 494/43; 435/173; 494/10
[58] Field of Search ....................... 494/43, 22, 23, 25, 494/27, 35, 37, 42, 85, 10, 16; 435/173

[56] References Cited

U.S. PATENT DOCUMENTS

| | | | |
|---|---|---|---|
| 3,785,549 | 1/1974 | Latham, Jr. | 233/23 |
| 3,927,826 | 12/1975 | Anderson et al. | 233/11 |
| 4,087,327 | 5/1978 | Feder et al. | 195/1.7 |
| 4,283,276 | 8/1981 | Grant | 494/43 |
| 4,346,172 | 8/1982 | Swartz | 435/173 |
| 4,350,283 | 9/1982 | Leonian | 494/43 |
| 4,414,106 | 11/1983 | Romanauskas | 209/155 |
| 4,418,150 | 11/1988 | Gunge | 435/256 |
| 4,441,972 | 4/1984 | Pohl | 204/183.1 |
| 4,531,932 | 7/1985 | Luppi et al. | 604/6 |
| 4,561,961 | 12/1985 | Hofmann | 204/299 R |
| 4,578,168 | 3/1986 | Hofmann | 204/299 R |
| 4,622,302 | 11/1986 | Sowers | 435/172.2 |

FOREIGN PATENT DOCUMENTS

3317415 A1 11/1984 Fed. Rep. of Germany .
3507398 A1 9/1986 Fed. Rep. of Germany .

Primary Examiner—Robert W. Jenkins
Attorney, Agent, or Firm—Lyman R. Lyon

[57] ABSTRACT

A method and apparatus for obtaining non-selective microsamples of intracellular material of a living cell while maintaining cell viability. The invention utilizes artificial gravity to effect power cell orientation prior to membrane poration; combined artificial gravity and electric field pulse to effect membrane poration; and artificial gravity to effect forced and controlled extraction of intracellular material subsequent to membrane poration.

3 Claims, 3 Drawing Sheets

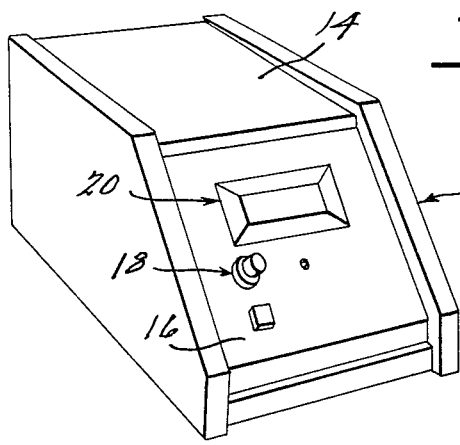
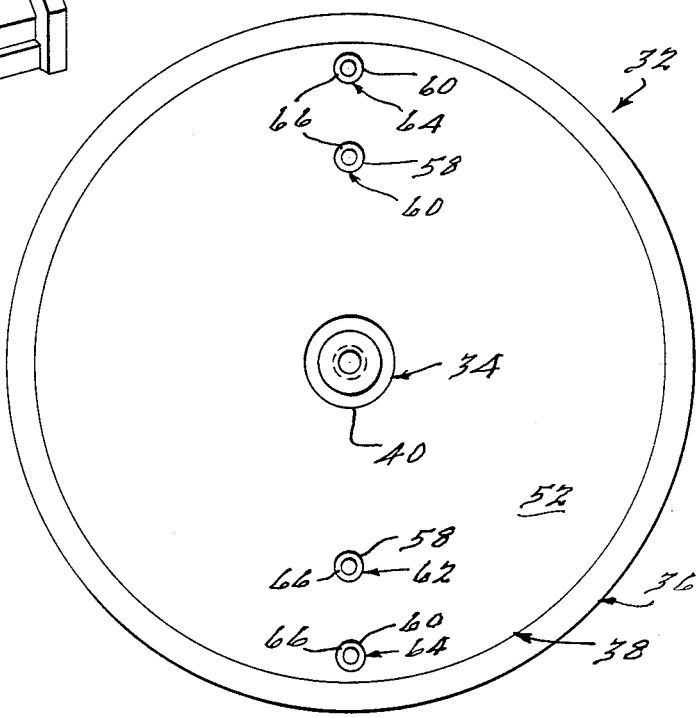
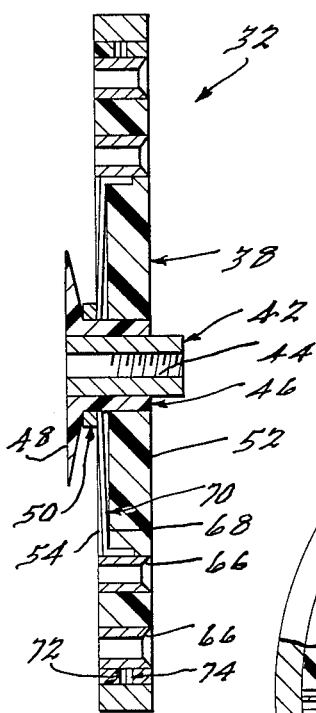
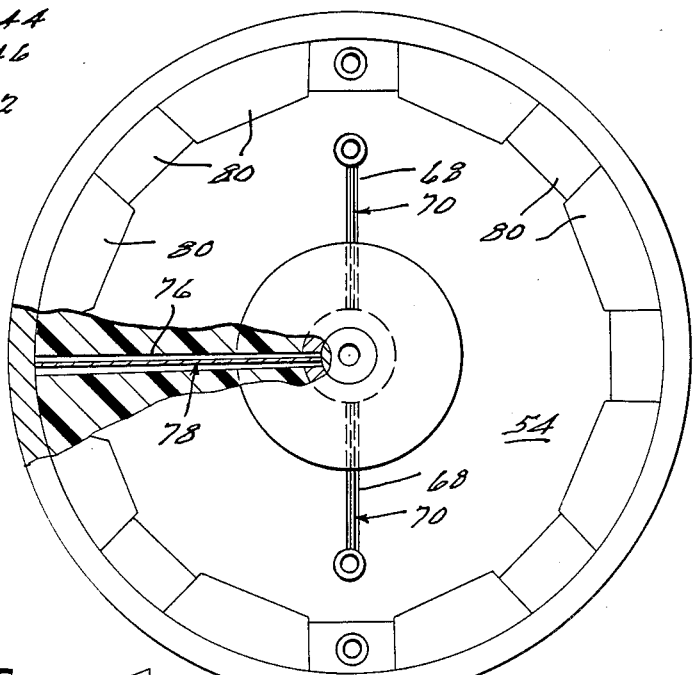

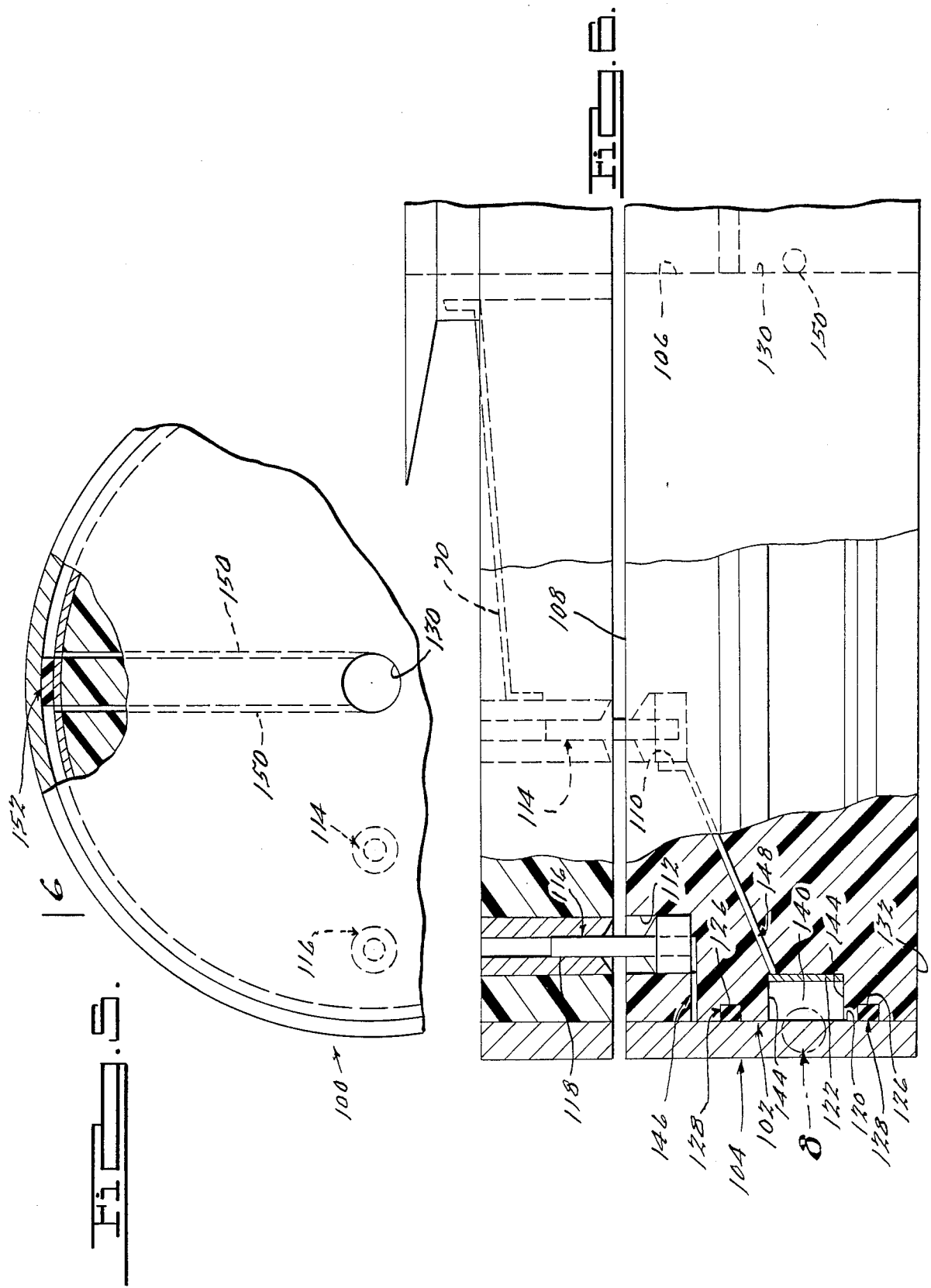

ARTIFICIAL GRAVITY INTRACELLULAR MOLECULAR EXTRACTION

BACKGROUND OF THE INVENTION

The invention relates to in vitro extraction of intracellular material while maintaining cell viability.

Living cells are implanted with new genes to form living factories producing specific molecules such as insulin, interferons, human growth hormone, etc. Unfortunately, even when such a "factory cell" produces large amounts of the desired molecules, most of them remain inside the membrane of the cell when it is alive. A variety of techniques have been developed to "harvest" these desired molecules.

The prior art teaches in vitro extraction of intracellular material by means of physical and/or chemical destruction of the cellular membrane, thereby releasing the cellular contents into the suspension medium, thereafter to be retrieved by conventional filtering techniques. Notwithstanding the substantial quantity of intracellular molecules obtained thereby, the cells are no longer viable biological entities subsequent to such treatment, and no additional molecular production is possible.

Alternatively, the prior art teaches the use of pulsed electric fields to create pores on the membranes of cells suspended in high-resistivity solutions through which intracellular material of limited dimension might diffuse, if given sufficient time. Unfortunately, the self-healing nature of cellular membranes rapidly eliminates membrane poration, thereby limiting the amount of time available for diffusion and, hence, limiting the quantity of intracellular material removed by this method. Moreover, the prior art fails to adequately separate the subject cells from each other prior to membrane poration, thereby promoting intercellular fusion rather than intracellular extraction.

SUMMARY OF THE INVENTION

It is the purpose of the instant invention to provide a method and apparatus for forced and controlled extraction of intracellular material from living cells without compromising cell viability.

It is also the purpose of the instant invention to provide a method and apparatus for generating cellular membrane poration, and maintaining such membrane porosity for substantial periods of time.

It is the further purpose of the instant invention to provide an improved method and apparatus for separation and orientation prior to such cellular membrane poration.

The instant invention accomplishes these purposes by subjecting the cells to an artificial gravity field before, and a continuously increasing artificial gravity field during and after application of an electric field pulse. The cells are separated and flattened by the initial artificial gravity field to facilitate cellular membrane poration; the combined effect of artificial gravity and electric field pulse produces simultaneous piercing of the cellular membrane; and cellular membrane poration is maintained and controlled, and extraction of intracellular material enhanced and controlled, by the intracellular pressure generated in response to the increasing artificial gravity field. Moreover, the controlled extraction of intracellular material is followed by application of a constant artificial gravity field which allows membrane resealing, thereby ensuring cell viability and allowing for the return of the cells to the culture medium for further molecule production.

Specifically, the method of the instant invention for extracting intercellular material from living cells comprises the following steps:

1. A non-continuous single-thickness layer of cells is centrifugally deposited on an electrode forming the radially outward surface of a centrifuge chamber containing a poration medium of low ionic conductivity. The electrode surface is provided with a radius of curvature equal to the distance from the surface to the rotational axis of the centrifuge rotor. The arcuate electrode surface prevents undesirable lateral compression among subject cells.

2. The angular velocity of the centrifuge rotor containing a plurality of centrifuge chambers is adjusted to provide an artificial gravity field sufficient to compress the cells against the electrode forming the radially outward surface of the centrifuge chamber. Such compression causes a distortion of the normal shape of the membranes of the cells, and, as cellular volume remains essentially constant notwithstanding slight volumetric reduction due to osmosis, the cellular membrane will be placed in tension and the intracellular pressure greatly increased. The tensioning of the cellular membrane in turn facilitates poration by action of an electric field pulse, since the magnitude of the electric field pulse required to pierce the membrane is reduced by the potential energy added by artificial gravity.

3. During the porating phase, the angular velocity of the centrifuge rotor is gradually and continuously increased. The electric field pulse is produced by an electric field generated between the first electrode comprising the radially outward surface of the centrifuge chamber, and a second electrode of suitable configuration placed radially inward of the first electrode. The combined effect of artificial gravity and electric field pulse produces a simultaneous piercing of each cellular membrane along the points thereof perpendicular to the lines of the electric field.

4. Once membrane poration is achieved, the continuously increasing angular velocity of the centrifuge rotor provides an increasing artificial gravity field within the centrifuge chamber. The resulting increasing intracellular pressure generated in response to the increasing artificial gravity field continuously forces intracellular material through the pores formed in the cellular membranes. The out-going flow of intracellular material in turn maintains membrane porosity by preventing the membrane periphery of the pores from closing together, a pre-condition to membrane self-healing, thereby allowing further amounts of intracellular material to exit the cells. The rate of molecular extraction is controlled by adjustment of the angular acceleration of the centrifuge rotor.

5. The extraction phase is completed when the angular velocity of the centrifuge rotor, and, hence, the artificial gravity field within the centrifuge chamber, is held for a time at a constant value. The intracellular pressure equalizes with the now constant chamber pressure. The out-going flow of intracellular material through the membrane pores ceases, as there is no longer a forcing pressure differential across the membrane induced by a continuously increasing artificial gravity field. The membrane periphery of the pores is thereby allowed to close naturally, and the membranes "heal" themselves, thereby sealing the pores.

6. The centrifuge rotor is allowed to coast to a stop, and the extracted intracellular material may be removed from the poration medium by conventional means. Agitation of the medium prior to removal may suspend or dissolve extracted material where the material exhibits a tendency to remain on the exterior surface of the cellular membranes.

BRIEF DESCRIPTION OF THE DRAWINGS

FIG. 1 is a perspective view of a centrifuge constructed in accordance with the present invention.

FIG. 2 is a top view of the centrifuge rotor assembly.

FIG. 3 is a sectional view of the rotor assembly taken along line 3—3 of FIG. 2

FIG. 4 is a bottom view of the rotor assembly of FIG. 2.

FIG. 5 is a top view of a centrifuge chamber assembly wherein cells are placed.

FIG. 6 is a side view, broken away in part for clarity, and taken in the direction of arrow 6 of FIG. 5, of the chamber assembly of FIG. 5 engaged with the rotor assembly of FIG. 2.

DETAILED DESCRIPTION OF THE PREFERRED EMBODIMENT OF THE INVENTION

Figure 8:
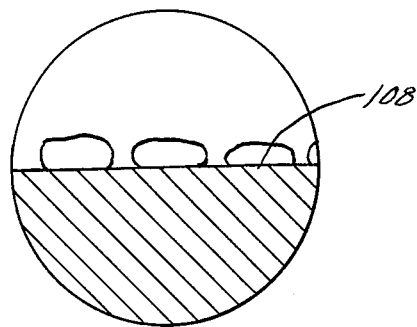
FIG. 8 is an illustration of cells centrifugally deposited in a non-continuous layer upon the surface of the radially outward electrode of the chamber assembly within circle 6 of FIG. 5.

FIG. 1 shows a centrifuge 10 embodying the present invention. The centrifuge housing 12 includes a circular rotor chamber 14 and a control panel 16 having a rotor assembly angular velocity control knob 18 and a rotor assembly angular velocity indicator 20. An electric motor (not shown) is disposed internally of the housing 12, having a threaded shaft (not shown) formed of electrically conductive material protruding within the center of the rotor chamber 14, whereupon a rotor assembly 24 is secured.

The rotor assembly 32 shown in FIG. 2 comprises a hub sub-assembly 34, a cylindrical peripheral wall 36 sharing the same longitudinal axis therewith, and a circular disk 38 defining a continuous radially outwardly extending surface between the hub sub-assembly 34 and the peripheral wall 36, the disk 38 being concentric with, and in the plane normal to the longitudinal axis of, the hub sub-assembly 34.

Referring to FIG. 3, the hub sub-assembly 34 comprises an inner cylinder 42, formed of electrically conductive material and having a circular longitudinal threaded aperture 44; an outer cylinder 46, concentric with the first, formed of an insulating material, having a central longitudinal aperture wherein the inner cylinder 42 is press-fit, and having one end supplied with a radially outwardly extending flange 48; and a ring 50, concentric with inner cylinder 42 and outer cylinder 46, formed of electrically conductive material, having a central longitudinal aperture wherein the outer cylinder 46 is press-fit.

As seen in FIG. 2, an annular cylindrical peripheral wall 36, formed of electrically conductive material such as steel, encompasses the entire rotor assembly 32. The peripheral wall 36 is of sufficient thickness to sustain the centrifugal forces and provide a suitably balanced rotor assembly 32.

Referring again to FIG. 3, the circular disk 38 which defines the continuous radially outwardly extending surface of the rotor assembly 32 is characteristically formed of an insulating material, such as a polymeric substance. A central circular aperture 40 whose longitudinal axis is normal to the plane of the disk 38 is formed therein wherein the outer cylinder 46 of the hub sub-assembly 34 is press-fit. The ring 50 of the hub sub-assembly 34 is thereby placed contiguous with both the flange 48 of the outer cylinder 46 and the underside 52 of the disk 38. After assembly, the longitudinal end of the outer cylinder 46 opposite the one supplied with flange 48 is flush with the top surface 52 of the disk 38. The longitudinal end of the inner cylinder 42, however, does protrude from the top surface 52 of the disk 38. The disk 38 in turn is press-fit into the peripheral wall 36 so that the underside 54 of the disk 38 is flush with both longitudinal ends of the peripheral wall 36.

As seen in FIG. 2, the surface of the disk 38 includes a plurality of cylindrical retaining holes 58 and 60 placed in radially-aligned pairs, with the radial distance from the longitudinal axis of the hub sub-assembly 34 remaining constant for each inner retaining hole 58 and each outer retaining hole 60 of each pair. FIG. 3 shows each retaining hole 58 and 60 comprising a central longitudinal aperture, whose axis is parallel to that of the hub sub-assembly 34, and a cylindrical lining 62 and 64, formed of electrically conductive material, having a central longitudinal aperture whose axis is also parallel to that of the hub sub-assembly 34. The longitudinal end of the cylindrical lining 62 and 64 nearest the top surface 52 of the disk 38 is supplied with a chamfer 66 to aid insertion of a retaining pin 114 and 116 therein.

As seen in FIG. 4, a channel 68 is formed in the underside 54 of the disk 38, extending from each inner retaining hole 58 radially inward to a point having a diameter equal to the inner diameter of the ring 50. A wire 70 is disposed therein, having its ends secured to the inner retaining hole lining 62 and the ring 50, respectively.

As seen in FIG. 3, an aperture 72 is formed in the peripheral edge of the disk 38 at a point radially outward of each outer retaining hole 60, extending radially inward therefrom in the plane of the disk 38. The aperture 72 is of sufficient depth so as to intersect the outer retaining hole 60. A wire 74 is internally disposed therein, having its ends secured to the peripheral wall 36 and the outer retaining hole lining 64, respectively, upon assembly.

As shown in cut-out in FIG. 4, a pair of diametrically opposed apertures 76 is formed in the peripheral edge of the disk 38 extending radially inward in the plane thereof with sufficient depth so as to interest the central aperture 40 formed therein and penetrate through the outer cylinder 46 of the hub sub-assembly 34. An electrically conductive rod 78 is internally disposed therein, having its ends secured to the peripheral wall 36 and the inner cylinder 42, respectively, upon assembly.

FIG. 4 additionally shows a plurality of contiguous alternating reflective and nonreflective surface markings 80 applied to the underside 54 of the rotor assembly 32. The markings 80 are used in conjunction with the angular velocity indicator 20 through use of a digital optical speed sensor (not shown).

Referring to FIGS. 5 and 6, a cell chamber assembly 100 comprises a circular disk 102, defining a continuous radially outwardly extending surface, and a cylindrical outer wall 104, concentric and coplanar therewith. The disk 102 is characteristically formed of an insulating material, such as a polymeric substance. A shallow central circular aperture 106 whose longitudinal axis is normal to the plane of the disk 102 is formed in the underside 108 thereof, wherein the protruding longitudinal end of the inner cylinder 42 of the rotor assembly 32 is inserted, upon engagement between the cell chamber assembly 100 and the rotor assembly 32.

The underside 108 of the disk 102 is provided with a plurality of circular apertures 110 and 112, wherein cylindrical retaining pins 114 and 116, formed on an electrically conductive material, are press-fit. Each retaining pin 114 and 116 has a cylindrical projection 118 extending beyond the underside 108 of the disk 102, and the apertures 110 and 112 are so positioned so as to allow insertion of each cylindrical projection 118 into the corresponding retaining hole lining 58 and 60 of the rotor assembly 32 upon engagement thereof, thereby providing positive electrical contact therebetween.

As shown in FIG. 6, a groove 122 is formed in the longitudinal center of the circumferential surface 120 of the disk 102, wherein an annular cylindrical electrode 124 is disposed. O-ring grooves 126 longitudinally displaced from the centered groove 122 in both directions are also formed in the circumferential surface 120 of the disk 102, and O-rings 128 disposed therein.

A second shallow central circular aperature 130 is formed in the disk 102 on the surface 132 opposite that into which the first shallow central circular aperture 106 is formed, the cavity formed thereby being completely isolated from that of the first aperture 106.

The cylindrical outer wall 104, characteristically formed of stainless steel, has a length along its longitudinal axis equal to that of the disk 102, and its longitudinal ends are positioned flush with the surfaces 108 and 132 thereof upon assembly by press-fitting. A cell chamber 140 is thus defined by the radially inward machined surface 142 of the outer wall 104, the radially outward surface of electrode 124, and the radially outwardly extending surfaces 144 of the longitudinally centered circumferential groove 122. The outer wall 104 serves as a second electrode within the cell chamber 140, thereby allowing the generation of an electric field between the electrode 124 and the outer wall 104. A wire 146, disposed internally of the disk 102, electrically connects the outer wall 100 to the inboard end of each outer retaining pin 116. Similarly, a wire 148 electrically connects the electrode 124 to the inboard end of each inner retaining pin 114.

As shown in hidden lines in FIG. 5, a pair of parallel spaced passages 150 are provided within the disk 102 extending from the aperture 130 to the cell chamber 140. As shown in cut-out in FIG. 5, a silicone plug 152 is placed within the cell chamber 140 between the passages 150, thereby sealing the shorter circumferential chamber path between the passages 150. Fluid introduced into one of the passages 150 is thus conducted through the cell chamber 140 along the longer circumferential chamber path between the passages 150, and then out the other of the passages 150.

Figure 7:
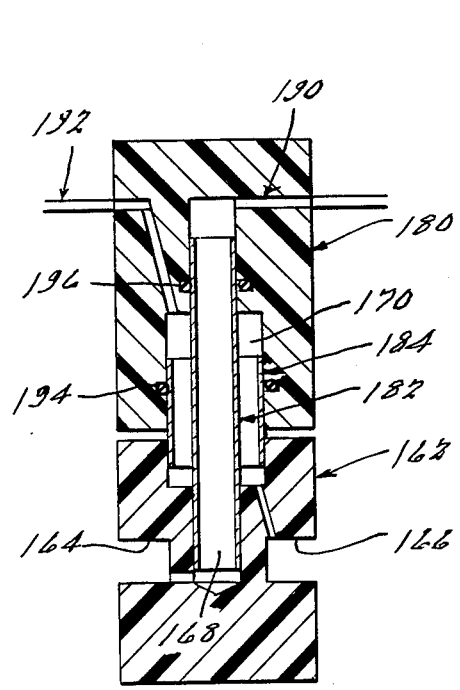
FIG. 7 is an elevational view of a slip port mechanism for the addition or removal of cells from the chamber assembly.

As best seen in FIG. 7, a rotary slip port mechanism 160 comprises a rotary lower element 162 that is fixedly press fit into aperture 130 of the cell chamber assembly 100. The element 162 has a pair of laterally extending ports 164 and 166 that register with the passages 150 in the disk 102. The port 164 communicates with a central passage 168, and the port 166 communicates with an annular passage 170.

A fixed upper element 180 is connected to the lower element 162 by a pair of sleeves 182 and 184, each of which is press fit into the lower element 162 so as to rotate therewith. The sleeve 182 extends upwardly to define the central passage 168 which, in turn, communicates with an inlet tube 190. The sleeve 184 extends upwardly into the fixed element 180 to define the annular passage 170 which communicates with an outlet tube 192. The sleeves 182 and 184 are sealed relative to the fixed element 180 by a pair of O-rings 194 and 196, respectively.

Although press-fitting was employed in the assembly of the preferred embodiment disclosed hereinabove, it may be readily appreciated that any suitable fastening means may be employed to secure assembly components together.

The operation of the centrifuge 10 in accordance with the method disclosed hereinabove for extraction of the intracellular material of mammalian cells is as follows:

A sterilized cell chamber assembly 100, having a rotary slip port 160 press-fit therein, is placed in contiguous engagement with a rotor assembly 32. The rotor assembly 32 is then mounted within the rotor chamber 14 of the centrifuge 10 upon the electrically conductive shaft of the electric motor housed therein (not shown). An electrical signal applied to the shaft is conducted to the outer wall 104 of the cell chamber assembly 100 via the inner cylinder 42, rod 78, peripheral wall 36, wire 74, outer retaining hole lining 64, outer retaining pin 116, and wire 146. An arcless brush (not shown) is placed in contact with the ring 50 of the rotor hub sub-assembly 26 to complete the electrical circuit leading to the electrode 124 of the cell chamber assembly 100 via wire 70, inner retaining hole lining 62, inner retaining pin 114, and wire 140.

The culture medium containing the cells in suspension is mixed with a poration medium such as 0.35 M sucrose in deionized water. The cells, suspended in the resultant mixture, are fed under pressure into the cell chamber 140 via the inlet tube 190, passage 168, port 164, and passage 150 of the cell chamber assembly 100. The complete filling of the cell chamber 140 is assured when the cell suspension mixture begins to exit the other passage 150 of the cell chamber 100. Cells may be concomitantly removed from the cell chamber 140 through a passage 150, port 166, passage 170 and exit tube 192. It is to be noted that the centrifuge 10 of the instant invention lends itself to batch or continuous operation by use of the slip port mechanism 160.

In order to maximize the extraction of intracellular material, it is important that sufficiently few cells are introduced thereby into the cell chamber 140 so as not to form a continuous single-thickness layer on the radially inward surface 142 of the outer wall 104 (hereinafter electrode surface 142) upon centrifugation. Undesirable lateral compression of cells is thereby avoided, allowing for maximum distortion of the cellular membrane upon further centrifugation. Multiple-thickness layers of cells formed upon the electrode surface 142 must be avoided, as "point-fusion" will be generated between cells contacting along the radial lines of the cell chamber assembly 100 upon the application of an electric field pulse. Since the amplitude of electric field pulse required for cellular membrane poration greatly exceeds that required for intercellular fusion, the point-fused fusion products will be initially porated as well. As the point-fused fusion products have increased membrane surface with which to absorb the increasing hydrostatic pressure during the initial stages of the extraction phase, there would be no out-going flow of intracellular material through the pores additionally formed in the membrane. A premature healing of the of cellular membrane would occur, thereby greatly limiting the quantity of intracellular material extracted.

Centrifugation begins as the rotor assembly 32 begins to rotate. A slow angular velocity is initially prescribed to transport the suspended cells to the electrode surface 142. The amount of time required to deposit the cells against the electrode surface 142 varies inversely with square of the angular velocity of the cell chamber assembly 100.

When the cells have been deposited against the surface 108 of the outer electrode 100, the resistivity of the porating medium may be measured by examining the resistance across the inner cylinder 34 and the ring 42, both of the hub sub-assembly 26, as they are electrically connected to the outer electrode 100 and the inner electrode 102, respectively. It will be seen that this value of medium resistivity may be used to estimate the quantity of intracellular material extracted by the instant method.

During the cell compression phase, the angular velocity of the rotor assembly is adjusted to a predetermined value by means of adjustment of the angular velocity control knob 18 while viewing the angular velocity indicator 20. The artificial gravity field generated by such rotation flattens the cells against the electrode surface 142, as illustrated in FIG. 8. As cell volume remains essentially constant, notwithstanding slight reduction of cell volume through osmosis, the membranes of the cells will be placed in tension and the cells internally pressurized. This tensioning of the cellular membrane in turn facilitates membrane poration by action of an electric field pulse, since the magnitude of the pulse required to pierce the membrane is reduced thereby.

Figure 9:
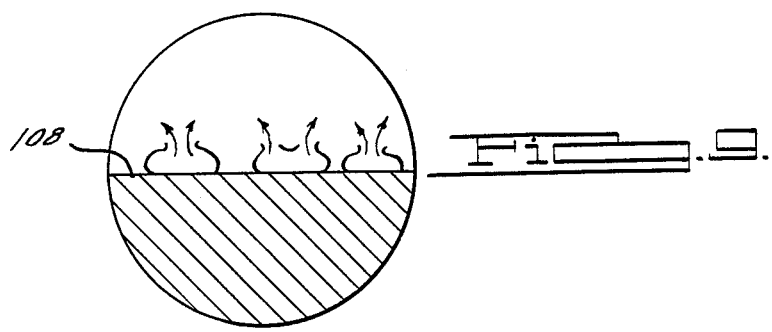
FIG. 9 is an illustration similar to that of FIG. 8 of porated cells experiencing increasing chamber hydrostatic pressure subsequent to application of electric field pulse.

As the porating phase begins, the angular velocity of the centrifuge rotor assembly 32 is gradually and continuously increased. The electric field pulse is then generated between the electode 124 and the outer wall 104. The combined effect of artificial gravity and electric field pulse produces simultaneous piercing of each cellular membrane along the radially extending lines of the centrifuge, as illustrated in FIG. 9.

Once membrane poration is achieved, the extraction phase begins. The continuously increasing angular velocity of the centrifuge rotor assembly 32 provides an ever increasing artificial gravity field within the cell chamber 140. The resulting increasing pressure within the cell chamber 140 further distorts the cellular membranes, thereby generating increased intracellular pressure. The resulting pressure differential continuously forces intracellular material through the pores formed in the cellular membranes, as illustrated by arrows in FIG. 9. The out-going flow of intracellular material in turn maintains cellular membrane porosity by preventing pore closure/healing, thereby allowing further quantities of intracellular material to exit the cells. The rate of extraction is controlled by adjustment of the angular acceleration of the cell chamber assembly 100. In that the medium containing the extricated material has greater ionic conductivity than the original porating medium, the amount of intracellular material extracted may be estimated by examining the change in the resistivity of the porating medium, as measured across the inner cylinder 42 and the ring 50, both of the rotor hub sub-assembly 34.

Figure 10:
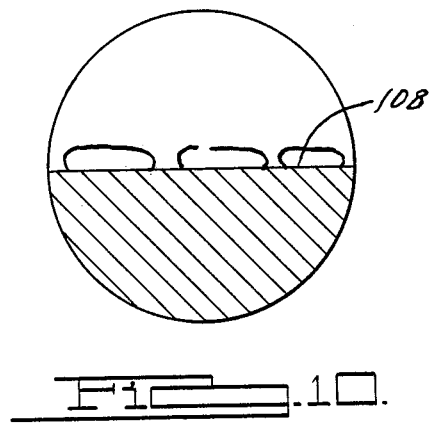
FIG. 10 is an illustration similar to that of FIG. 8 of subject cells whose membranes are undergoing self-healing upon the stabilization of hydrostatic pressure within the chamber.

The extraction phase is completed when the angular velocity of the centrifuge rotor assembly 32 is held for a time at a constant value. The intracellular pressure equalizes with the now constant pressure of the cell chamber 140. There is no longer a pressure differential to force and control the flow of intracellular material through the pores in the cellular membrane. As there is no longer an out-going flow of material to prevent pore closure, the cellular membranes begin to close and "heal" themselves, thereby eliminating membrane poration, as illustrated in FIG. 10.

In the final removal phase, the cell chamber assembly 100 is allowed to coast to a complete stop. The contents of the cell chamber 140 is removed therefrom by purging the cell chamber 140 by feeding culture medium under pressure through the rotary slip port 160 and into a passage 150 of the cell chamber assembly 100. The angular momentum of the cells tends to cause cell shifting upon slowing of the cell chamber assembly 100, producing agitation of the medium within the cell chamber 140 and helping to suspend or dissolve therein any extracted material which might otherwise exhibit a tendency to remain on the exterior surface of the cellular membrane.

While the preferred embodiment of the invention has been disclosed, it should be appreciated that the invention is susceptible of modification without departing from the spirit of the invention or the scope of the subjoined claims.

I claim:

1. A centrifuge for producing an artificial gravity field to effect intracellular molecular extraction comprising
   a rotor,
   an annular chamber in said rotor at the periphery thereof,
   a first electrode in said chamber forming a radially inner surface thereof,
   a second electrode in said chamber forming a radially outer surface thereof, and
   means for applying an electrical potential across said first and second electrodes of the chamber.

2. The centrifuge of claim 1 wherein the radially outer surface of said rotor chamber comprises a section of a right circular cylinder.

3. The centrifuge of claim 1 including
   a barrier in said chamber,
   an inlet on one side of said barrier for the admission of cells, and an outlet on the other side of said barrier for the removal of cells;
   means coupling said inlet and said outlet to a central rotary element; and
   means coupling said rotary element to a fixed element for adding and removing cells in liquid suspension from said chamber.

* * * * *